United States Patent
Sakuma et al.

(10) Patent No.: US 8,409,480 B2
(45) Date of Patent: Apr. 2, 2013

(54) PROCESS FOR PREPARING ORGANIC ALKALI METAL COMPOUND AND ORGANIC TRANSITION METAL COMPOUND

(75) Inventors: Atsushi Sakuma, Ichihara (JP); Munehito Funaya, Ichihara (JP)

(73) Assignee: Mitsui Chemicals, Inc., Tokyo (JP)

( * ) Notice: Subject to any disclaimer, the term of this patent is extended or adjusted under 35 U.S.C. 154(b) by 322 days.

(21) Appl. No.: 12/745,868

(22) PCT Filed: Dec. 2, 2008

(86) PCT No.: PCT/JP2008/071908
§ 371 (c)(1),
(2), (4) Date: Jun. 2, 2010

(87) PCT Pub. No.: WO2009/072505
PCT Pub. Date: Jun. 11, 2009

(65) Prior Publication Data
US 2012/0049391 A1    Mar. 1, 2012

(30) Foreign Application Priority Data
Dec. 4, 2007 (JP) ................................. 2007-313007

(51) Int. Cl.
*C07F 3/04* (2006.01)
(52) U.S. Cl. ..................................... 260/665 R; 585/931
(58) Field of Classification Search .................. None
See application file for complete search history.

(56) References Cited

U.S. PATENT DOCUMENTS

| | | | | |
|---|---|---|---|---|
| 4,006,187 A | * | 2/1977 | Kamienski et al. | 564/305 |
| 5,565,534 A | * | 10/1996 | Aulbach et al. | 526/160 |

FOREIGN PATENT DOCUMENTS

| | | |
|---|---|---|
| EP | 0 661 300 B1 | 7/1995 |
| JP | 08-208733 A | 8/1996 |
| JP | 11-012290 A | 1/1999 |
| JP | 2001-011087 A | 1/2001 |
| JP | 3176092 B2 | 4/2001 |
| JP | 3320619 B2 | 6/2002 |
| JP | 3713405 B2 | 8/2005 |

OTHER PUBLICATIONS

"Organometallic Chemistry, Lectures of New Experimental Chemistry 12 (Yuki Kinzoku Kagaku, Shin Jikken Kagaku Koza)", The Chemical Society of Japan, 1975, pp. 48-51 with partial translation (1 pg).

Tamm et al., "Synthesis and Reactivity of Silicon- and Germanium-Bridged *Ansa*-Cycloheptatrienyl-Cyclopentadienyl Titanium Complexes", Organometallics, 2007, vol. 26, pp. 417-424.

Schlosser, Manfred, "Superbases for Organic Synthesis", Pure & Appl. Chem., 1988, vol. 60(11), pp. 1627-1634.

Communication (Supplementary EP Search Report) in EP Appln No. 08 85 6231.9 dated Jan. 13, 2012.

Fraenkel, G. et al. "Radicals from the Reaction of Hindered t-Benzyllithium Compounds with $O_2$", J.C.S. Chem. Comm., 1980, pp. 55-56.

International Search Report PCT/JP2008/071908 dated Feb. 20, 2009.

Thomas E. Ready et al., "Alkyl-substituted indenyl titanium precursors for syndiospecific Ziegler-Natta polymerization of styrene", Journal of Organometallic Chemistry 519 (1996) pp. 21-28.

* cited by examiner

*Primary Examiner* — Sudhakar Katakam
(74) *Attorney, Agent, or Firm* — Foley & Lardner LLP

(57) ABSTRACT

[Problem] To provide a preparation process by which an organic alkali metal compound is obtained in a high yield and a process for preparing an organic transition metal compound using the organic alkali metal compound. [Means to solve the problem] A process for preparing an organic alkali metal compound, which is characterized by adding a compound represented by the following formula (2) in the reaction of an active proton-containing compound represented by the following formula (1) with an alkali metal compound.

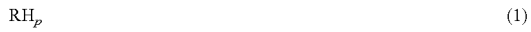

$$RH_p \qquad (1)$$

In the formula (1), R is a hydrocarbon group or an amino group and may contain a halogen atom, a silicon atom, an oxygen atom or a nitrogen atom, H is an active proton, and p is the number of hydrogen atoms abstracted in the reaction with the alkali metal compound.

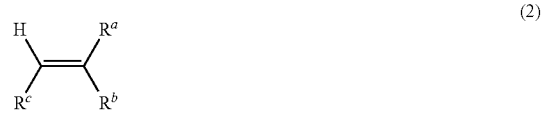

(2)

In the formula (2), $R^a$ to $R^c$ are each an atom or a group selected from a hydrogen atom, a hydrocarbon group, a heteroatom-containing group and a silicon-containing group and may be the same as or different from each other, and the neighboring substituents may be bonded to each other to form a ring.

6 Claims, No Drawings

PROCESS FOR PREPARING ORGANIC ALKALI METAL COMPOUND AND ORGANIC TRANSITION METAL COMPOUND

TECHNICAL FIELD

The present invention relates to a process for preparing an organic alkali metal compound and a process for preparing an organic transition metal compound using the organic alkali metal compound.

BACKGROUND ART

Many processes for synthesizing organometallic compounds of alkali metals such as lithium, sodium and potassium have been developed so far, and there are known, for example, synthesis of butyllithium by the reaction of butyl bromide with metallic lithium (reaction (I), non-patent document 1):

$$C_4H_9Br + 2Li \rightarrow C_4H_9Li + LiBr \quad (I), \text{ and}$$

synthesis of benzyllithium by the reaction of tribenzylchlorostannane with methyllithium (reaction (II), non-patent document 1):

$$(C_6H_5CH_2)_3SnCl + 4CH_3Li \rightarrow 3C_6H_5CH_2Li + (CH_3)_4Sn + LiCl \quad (II).$$

Most of the alkali metal compounds synthesized as above can produce novel organometallic reaction agents by the reaction of them with organic compounds having active proton, and therefore, they have been used for various purposes. For example, there can be mentioned production of a so-called metallocene compound using a cyclopentadienyl group as a ligand, which is well known as an organic transition metal compound, particularly an olefin polymerization catalyst. Since the metallocene compound has features that its polymerization activity is extremely high and a polymer having a narrow molecular weight distribution is obtained, studies of various synthetic processes have been made so far. Of these, a great number of processes wherein a ligand having an active proton is deprotonated by such an alkali metal compound as mentioned above and further allowed to react with a metal halide or the like have been particularly reported (patent documents 1 to 3).

In such syntheses of metallocene compounds, it has been frequently observed that deprotonation by the alkali metal compound does not proceed depending upon the structure of the ligand, and in such cases, the intended deprotonation of the ligand is promoted by using a coordination solvent such as tetrahydrofuran (THF) or by adding N,N, N',N'-tetramethylethylenediamime (TMEDA) as a chelating agent for the purpose of enhancing basicity of the alkali metal reagent (patent document 4, non-patent document 2).

However, it is known that amines such as TMEDA and THF have problems such as evil influence on the subsequent step and remaining of them in the end product, and for example, in the production of a metallocene compound, instability of the resulting metallocene compound and lowering of activity in the polymerization reaction have been reported (patent documents 5 and 6). Further, in such compounds, there are compounds having strong toxicity and compounds having carcinogenesis, so that development of lowly hazardous substitute compounds has been promoted.

Moreover, it has been reported that a mixture of alkyllithium and potassium alkoxide exhibits extremely strong basicity (non-patent document 3).

The organopotassium compound produced by this process, however, is very sensitive to air and moisture. It is known that lithium alkoxide formed as a by-product becomes a cause of side reaction when it remains in the subsequent step. For example, in the production of a metallocene compound, the lithium alkoxide causes lowering of yield due to side reaction with a transition metal compound that is a raw material or causes marked decrease of polymerization activity due to incorporation into the resulting metallocene compound. On that account, after treatments of many steps, such as solvent cleaning and extraction, become necessary.

Accordingly, development of processes for preparing an organic alkali metal compound and an organic transition metal compound such as a metallocene compound without causing such problems has been desired.

Patent document 1: Japanese Patent No. 3,176,092
Patent document 2: Japanese Patent Laid-Open Publication No. 12290/1999
Patent document 3: Japanese Patent No. 3,320,619
Patent document 4: Japanese Patent Laid-Open Publication No. 208733/1996
Patent document 5: Japanese Patent No. 3,713,405
Patent document 6: Japanese Patent Laid-Open Publication No. 11087/2001
Non-patent document 1: the Chemical Society of Japan, Ed., "Yuki Kinzoku Kagaku (Organometallic Chemistry) (Shin Jikken Kagaku Koza (Lectures of New Experimental Chemistry) 12)", Maruzen (1975)
Non-patent document 2: Organometallics, 2007, 26, 417-424
Non-patent document 3: Pure & Appl. Chem., 1988, 60, 1627-1634

DISCLOSURE OF THE INVENTION

Problem to be Solved by the Invention

It is an object of the present invention to provide a process for preparing a novel organic alkali metal compound and to provide a process for preparing an organic transition metal compound using the compound obtained by the process.

Means to Solve the Problem

The above object is achieved by adding an olefin compound represented by the following formula (2) in the reaction of an active proton-containing compound represented by the following formula (1) with an alkali metal compound.

$$RH_p \quad (1)$$

In the formula (1), R is a hydrocarbon group or an amino group and may contain a halogen atom, a silicon atom, an oxygen atom or a nitrogen atom, H is an active proton, and p is the number of hydrogen atoms abstracted in the reaction with the alkali metal compound.

In the formula (2), $R^a$ to $R^c$ are each an atom or a group selected from a hydrogen atom, a hydrocarbon group, a heteroatom-containing group and a silicon-containing group and may be the same as or different from each other, and the neighboring substituents may be bonded to each other to form a ring,

Effect of the Invention

By the present invention, an organic alkali metal compound is obtained in a high yield, and use of the compound obtained by the process makes it possible to prepare an organic transition metal compound that has been difficult to prepare so far. Further, by the use of a compound of low toxicity, an organic alkali metal compound can be prepared safely, and therefore, the present invention is of industrially great value.

BEST MODE FOR CARRYING OUT THE INVENTION

The active proton-containing compound represented by the aforesaid formula (1), the olefin compound represented by the aforesaid formula (2), the alkali metal compound for carrying out deprotonation and the organic alkali metal compound represented by the following formula (3) are described in order hereinafter. Subsequently, the process for preparing an organic alkali metal compound represented by the following formula (3), which is characterized by adding the olefin compound represented by the aforesaid formula (2) in the reaction of the active proton-containing compound represented by the aforesaid formula (1) with the alkali metal compound, and the process for preparing an organic transition metal compound represented by the following formula (6), preferably an organic transition metal compound (metallocene compound) represented by the following formula (7), by the reaction of the organic alkali metal compound with a transition metal compound represented by the following formula (5) are described in detail.

$$RN_p \quad (3)$$

In the formula (3), R is a hydrocarbon group or an amino group and may contain a halogen atom, a silicon atom, an oxygen atom or a nitrogen atom, N is an alkali metal atom, and p is the same value as in the aforesaid formula (1).

$$MZ_k \quad (5)$$

In the formula (5), M is a metal selected from Group 4 to Group 6 of the periodic table, Z is selected from a halogen atom, a hydrocarbon group, an anionic ligand and a neutral ligand capable of coordination by a lone pair in combination with the same or different atom, group or ligand, and k represents a valence of M and is an integer of 3 to 6.

$$R_rMZ_{(k-r \times p)} \quad (6)$$

In the formula (6), M is a metal selected from Group 4 to Group 6 of the periodic table, R is a hydrocarbon group or an amino group and may contain a halogen atom, a silicon atom, an oxygen atom or a nitrogen atom, Z is selected from a halogen atom, a hydrocarbon group, an anionic ligand and a neutral ligand capable of coordination by a lone pair in combination with the same or different atom, group or ligand, k represents a valence of M and is an integer of 3 to 6, r is a natural number of not more than k, p is the same value as in the aforesaid formula (1), and k, r and p have a relationship of $k \geq r \times p$.

$$L_mMQ_n \quad (7)$$

In the formula (7), M is a metal selected from Group 4 to Group 6 of the periodic table, L is a ligand having a cyclopentadienyl ring, m is an integer of 1 to 3, when plural L are present, they may be the same as or different from each other, plural L may be directly linked to each other or may be linked through a crosslinking group containing a carbon atom, a halogen atom, a silicon atom, a nitrogen atom, an oxygen atom, a sulfur atom or a phosphorus atom, Q is selected from a halogen atom, a hydrocarbon group, an anionic ligand and a neutral ligand capable of coordination by a lone pair in combination with the same or different atom, group or ligand, and n is an integer of 1 to 4.

The active proton-containing compound in the invention is a compound represented by the aforesaid formula (1) ($RH_p$). $RH_p$ means a compound having an active proton. The active proton-containing compound in the invention is preferably a compound having methine hydrogen or methylene hydrogen as an active proton, and is more preferably a compound containing a cyclopentadiene skeleton having methine hydrogen or methylene hydrogen as an active proton.

In the formula (1), R is a hydrocarbon group (e.g., monovalent hydrocarbon group) or an amino group and may contain a halogen atom, a silicon atom or a heteroatom (e.g., oxygen atom, nitrogen atom or the like). In the present invention, the active proton is defined as active hydrogen having an acid dissociation constant (pKa) of not more than 60, preferably not more than 42, more preferably not more than 39, particularly preferably not more than 35.

Examples of the hydrocarbon groups include straight-chain hydrocarbon groups, such as methyl group, ethyl group, n-propyl group, allyl group, n-butyl group, n-pentyl group, n-hexyl group, n-heptyl group, n-octyl group, n-nonyl group and n-decanyl group; branched hydrocarbon groups, such as isopropyl group, tert-butyl group, amyl group, 3-methylpentyl group, 1,1-diethylpropyl group, 1,1-dimethylbutyl group, 1-methyl-1-propylbutyl group, 1,1-propylbutyl group, 1,1-dimethyl-2-methylpropyl group and 1-methyl-1-isopropyl-2-methylpropyl group; cyclic saturated hydrocarbon groups, such as cyclopentyl group, cyclohexyl group, cycloheptyl group, cyclooctyl group, norbornyl group, adamantyl group, methylcyclohexyl group and methyladamantyl group; cyclic unsaturated hydrocarbon groups, such as phenyl group, tolyl group, naphthyl group, biphenyl group, phenanthryl group and anthracenyl group; cyclopentadienyl groups and their derivatives, such as cyclopentadienyl group, methylcyclopentadienyl group, n-butylcyclopentadienyl group, t-butylcyclopentadienyl group, 1,2-dimethylcyclopentadienyl group, 1-methyl-2-isopropylcyclopentadienyl group, 1,2,3-trimethylcyclopentadienyl group, tetramethylcyclopentadienyl group, pentamethylcyclopentadienyl group, indenyl group, 4,5,6,7-tetrahydroindenyl group, 2-methylindenyl group, 2-t-butylindenyl group, 4,5-benzindenyl group, 4-phenylindenyl group, azulenyl group, 2-methylazulenyl group, 2-phenylazulenyl group, 1,2-dimethylazulenyl group, 4,5,6,7-tetrahydroazulenyl group, fluorenyl group, 2,7-dimethylfluorenyl group, 3,6-dimethylfluorenyl group, 2,7-di-t-butylfluorenyl group, 3,6-di-t-butylfluorenyl group, benzofluorenyl group, dibenzofluorenyl group, octahydrodibenzofluorenyl group, octamethyloctahydrodibenzofluorenyl group and octamethyltetrahydrodicyclopentafluorenyl group; and saturated hydrocarbon groups substituted with cyclic unsaturated hydrocarbon groups, such as benzyl group, cumyl group, diphenylmethyl group, 1,1-diphenylethyl group and triphenylmethyl group.

The hydrocarbon group may be a hydrocarbon group wherein the above hydrocarbon groups given as examples are directly linked to each other or linked through a crosslinking group containing a carbon atom, a halogen atom, a silicon atom or a heteroatom (e.g., oxygen atom, nitrogen atom or the like).

Examples of the hydrocarbon groups wherein the above hydrocarbon groups are linked through a crosslinking group include bis(cyclopentadienyl)dimethylsilane, bis(indenyl)dimethylsilane, (cyclopentadienyl) (t-butylamino)dimethylsilane, bis(hydroazulenyl)dimethylsilane, 1-cyclopentadienyl-2-fluorenylethane and 2-cyclopentadienyl-2-fluorenylpropane.

Examples of the amino groups include methylamino group, ethylamino group, n-propylamino group, n-butylamino group, t-butylamino group, cyclohexylamino group, dimethylamino group, diethylamino group, di-n-propylamino group, di-n-butylamino group, di-t-butylamino group, methylphenylamino group, N-phenylcyclohexylamino group, diphenylamino group, 1-naphthylphenylamino group, pyrrolidyl group and piperidyl group.

The above hydrocarbon groups or amino groups may have, as a substituent, a halogen atom, a silicon atom, a heteroatom (e.g., oxygen atom, nitrogen atom or the like) or a group containing any of them. Examples of such substituents include halogen atoms, such as chlorine and fluorine; halogenated hydrocarbon groups, such as trichloromethyl group, chlorophenyl group, bromophenyl group, trifluoromethyl group, fluorophenyl group, pentafluorophenyl group and trifluoromethylphenyl group; hydrocarbon group-substituted silyl groups, such as trimethylsilyl group, triethylsilyl group, dimethylphenylsilyl group, diphenylmethylsilyl group and triphenylsilyl group; silyl group-substituted hydrocarbon groups, such as trimethylsilylmethyl, triphenylsilylmethyl, trimethylsilylphenyl and triphenylsilylphenyl; and heteroatom-containing groups, such as methoxy group, ethoxy group, phenoxy group, furyl group, N-methylamino group, N,N-dimethylamino group, N-phenylamino group, pyryl group and thienyl group.

Of the above hydrocarbon groups and amino groups, preferable are cyclopentadienyl groups and their derivatives, saturated hydrocarbon groups substituted with cyclic unsaturated hydrocarbon groups, and hydrocarbon groups containing a halogen atom, a silicon atom or a heteroatom.

In the formula (1), p is the number of active protons abstracted in the reaction with the later-described alkali metal compound. As the active proton abstracted in the reaction, one active proton may be present or plural active protons may be present in the compound.

The olefin compound added in the process for preparing an organic alkali metal compound according to the invention is a compound represented by the aforesaid formula (2).

In the formula (2), $R^a$ to $R^c$ are each an atom or a group selected from a hydrogen atom, a hydrocarbon group, a heteroatom-containing group and a silicon-containing group, preferably an atom or a group selected from a hydrogen atom, a hydrocarbon group and a silicon-containing group, and they may be the same as or different from each other, and the neighboring substituents may be bonded to each other to form a ring Examples of the hydrocarbon groups include straight-chain hydrocarbon groups, such as methyl group, ethyl group, n-propyl group, allyl group, n-butyl group, n-pentyl group, n-hexyl group, n-heptyl group, n-octyl group, n-nonyl group and n-decanyl group; branched hydrocarbon groups, such as isopropyl group, tert-butyl group, amyl group, 3-methylpentyl group, 1,1-diethylpropyl group, 1,1-dimethylbutyl group, 1-methyl-1-propylbutyl group, 1,1-propylbutyl group, 1,1-dimethyl-2-methylpropyl group and 1-methyl-1-isopropyl-2-methylpropyl group; cyclic saturated hydrocarbon groups, such as cyclopentyl group, cyclohexyl group, cycloheptyl group, cyclooctyl group, norbornyl group, adamantyl group, methylcyclohexyl group and methyladamantyl group; cyclic unsaturated hydrocarbon groups, such as phenyl group, tolyl group, naphthyl group, biphenyl group, phenanthryl group and anthracenyl group; and saturated hydrocarbon groups substituted with cyclic unsaturated hydrocarbon groups, such as benzyl group, cumyl group, 1,1-diphenylethyl group and triphenylmethyl group.

Examples of the heteroatom-containing groups include oxygen-containing groups, such as methoxy group, ethoxy group, phenoxy group and furyl group; nitrogen-containing groups, such as N-methylamino group, N, N-dimethylamino group, N-phenylamino group and pyryl group; and sulfur-containing groups, such as thienyl group.

Examples of the silicon atom-containing groups include hydrocarbon group-substituted silyl groups, such as trimethylsilyl group, triethylsilyl group, dimethylphenylsilyl group, diphenylmethylsilyl group and triphenylsilyl group; and silyl group-substituted hydrocarbon groups, such as trimethylsilylmethyl, triphenylsilylmethyl, trimethylsilylphenyl and triphenylsilylphenyl.

In the formula (2), it is preferable that at least one of $R^a$ to $R^d$ is a cyclic unsaturated hydrocarbon group, specifically an aryl group, more specifically a phenyl group, a tolyl group, a naphthyl group, a biphenyl group, a phenanthryl group or an anthracenyl group. It is more preferable that $R^a$ is an aryl group; it is still more preferable that $R^a$ is a phenyl group; and it is particularly preferable that $R^a$ is a phenyl group, $R^b$ is a methyl group, and $R^c$ is hydrogen.

In the present invention, the amount of the compound represented by the formula (2) added is in the range of 0.3 to 1.5 mol, preferably 0.5 to 1.3 mol, more preferably 0.9 to 1.1 mol, based on 1 mol of proton eliminated.

Examples of the alkali metal compounds for use in the invention include simple alkali metals, such as lithium, sodium and potassium; alkali metal hydrides, such as lithium hydride, sodium hydride and potassium hydride; alkali metal aromatic compounds, such as sodium-naphthalene; alkyl alkali metals, such as alkyllithium, alkylsodium and alkylpotassium; aryl alkali metals, such as aryllithium and arylpotassium; arylalkyl alkali metals, such as arylalkyllithium and arylalkylpotassium; and alkali metal amides, such as lithium amide, sodium amid and potassium amide.

A preferred embodiment of the alkali metal compound is a compound represented by the following formula (4), and a more preferred embodiment thereof is a lithium compound represented by the following formula (8).

$$AN \quad\quad (4)$$

In the formula (4), N is an alkali metal atom, specifically, lithium atom, sodium atom, potassium atom or cesium atom.

$$ALi \quad\quad (8)$$

In the formulas (4) and (8), A is a hydrocarbon group of 1 to 15 carbon atoms. Examples of such hydrocarbon groups include straight-chain hydrocarbon groups, such as methyl group, ethyl group, n-propyl group, allyl group, n-butyl group, s-butyl group, n-pentyl group, n-hexyl group, n-heptyl group, n-octyl group, n-nonyl group and n-decanyl group; branched hydrocarbon groups, such as isopropyl group, isobutyl group, tert-butyl group, amyl group and 3-methylpentyl group; cyclic saturated hydrocarbon groups, such as cyclopropyl group, cyclobutyl group, cyclopentyl group, cyclohexyl group, cycloheptyl group, cyclooctyl group and methylcyclohexyl group; cyclic unsaturated hydrocarbon groups, such as phenyl group, tolyl group, naphthyl group, biphenyl group, phenanthryl group and anthracenyl group;

and saturated hydrocarbon groups substituted with cyclic unsaturated hydrocarbon groups, such as benzyl group and cumyl group.

In the formulas (4) and (8), A is preferably a methyl group, a n-butyl group, a s-butyl group or a phenyl group, most preferably a n-butyl group.

The amount of the alkali metal compound used is in the range of 0.8 to 1.3 mol, preferably 0.9 to 1.1 mol, most preferably 1.0 to 1.1 mol, based on 1 mol of proton eliminated.

Examples of the solvents for use in the preparation of an organic alkali metal compound in the invention include hydrocarbons, e.g., aliphatic hydrocarbons, such as pentane, hexane, heptane, cyclohexane and decalin, and aromatic hydrocarbons, such as benzene, toluene and xylene; aliphatic ethers, such as diethyl ether, diisopropyl ether, tert-butyl methyl ether, cyclopentyl methyl ether and 1,2-dimethoxyethane; cyclic ethers, such as dioxane; and halogenated hydrocarbons, such as dichloromethane, chloroform and chlorobenzene. These solvents may be used after two or more kinds of them are mixed.

As the solvents for use in the invention, hydrocarbons or aliphatic ethers are preferable, and they can be used after they are mixed. The mixing ratio by volume between the hydrocarbons and the aliphatic ethers can be arbitrarily set to such an extent that the reaction of the alkali metal compound for carrying out deprotonation is not impaired. The mixing ratio of hydrocarbons/aliphatic ethers is in the range of preferably 100/0 to 0/100, more preferably 100/0 to 50/50, still more preferably 95/5 to 85/15. The deprotonation reaction in the invention is carried out at a temperature of −80 to 200° C., preferably −20 to 130° C., more preferably 20 to 90° C.

The organic alkali metal compound prepared as above can be used for the preparation of an organic compound that is generally prepared by the use of an organic alkali metal compound, for example, preparation of an alcohol from ketone or carboxylic acid, preparation of ketone by the reaction with carboxylic acid, etc.

Moreover, the organic alkali metal compound can be used for the preparation of an organometallic compound having, as its central metal, a typical metal or a transition metal element selected from Group 1 to Group 14 of the periodic table, such as magnesium, scandium, titanium, zirconium, hafnium, vanadium, chromium, molybdenum, tungsten, manganese, iron, ruthenium, cobalt, rhodium, nickel, palladium, copper, zinc, aluminum or tin.

Preferred examples of conversions into the organic transition metal compound are described in detail hereinafter. That is to say, the organic alkali metal compound represented by the aforesaid formula (3) can be effectively converted into an organic transition metal compound represented by the following formula (6) by the reaction with a transition metal compound represented by the following formula (5).

$$MZ_k \quad (5)$$

In the formula (5), M is an atom of Group 4 to Group 6 of the periodic table. Examples of such atoms include Group 4 metal atoms, such as titanium atom, zirconium atom and hafnium atom, Group 5 metal atoms, such as vanadium atom, niobium atom and tantalum atom, and Group 6 metal atoms, such as chromium atom, molybdenum atom or tungsten atom. Of these, preferable are titanium atom, zirconium atom, hafnium atom, vanadium atom, niobium atom and tantalum atom; more preferable are titanium atom, zirconium atom, hafnium atom and vanadium atom; still more preferable are Group 4 atoms of the periodic table, such as titanium atom, zirconium atom and hafnium atom; and most preferable are zirconium atom and hafnium atom. Z is selected from a halogen atom, a hydrocarbon group, an anionic ligand and a neutral ligand capable of coordination by a lone pair in combination with the same or different atom, group or ligand, and preferable is a halogen atom. k is an integer of 3 to 6, preferably 3 or 4, more preferably 4.

Preferred examples of the compounds represented by the formula (5) include trivalent or tetravalent titanium fluoride, chloride, bromide and iodide; tetravalent zirconium fluoride, chloride, bromide and iodide; tetravalent hafnium fluoride, chloride, bromide and iodide; and complexes of these compounds and ethers such as tetrahydrofuran, diethyl ether, dioxane and 1,2-dimethoxyethane.

$$R_r MZ_{(k-r \times p)} \quad (6)$$

In the formula (6), M is an atom of Group 4 to Group 6 of the periodic table similarly to PI in the formula (5). R is a hydrocarbon group or an amino group similarly to R in the formula (1) or the formula (3), and may contain a halogen atom, a silicon atom, an oxygen atom or a nitrogen atom. Z is selected from a halogen atom, a hydrocarbon group, an anionic ligand and a neutral ligand capable of coordination by a lone pair in combination with the same or different atom, group or ligand, similarly to Z in the formula (5). k represents a valence of M and is an integer of 3 to 6, preferably 3 or 4, more preferably r is a natural number of not more than k. p is the number of hydrogen atoms abstracted in the reaction of the active proton-containing compound represented by the formula (1) with the alkali metal compound, similarly to p in the formula (1) or the formula (3). r, k and p have a relationship of k≧r×p, and preferred combinations (r, k, p) are (1, 4, 2), (2, 4, 1), (1, 3, 1) and (2, 3, 1). When plural R are present, they may be the same as or different from each other. Plural R may be directly linked to each other or may be linked through a crosslinking group containing a carbon atom, a halogen atom, a silicon atom or a heteroatom (nitrogen atom, oxygen atom, sulfur atom, phosphorus atom or the like).

A preferred embodiment of the organic transition metal compound represented by the formula (6) is an organic transition metal compound represented by the following formula (7) (sometimes referred to as a "metallocene compound" in the following description).

$$L_m MQ_n \quad (7)$$

In the formula (7), M is the same as that in the formula (6), and is preferably an atom of Group 4 of the periodic table. L is a ligand having a conjugated 5-membered ring, such as (substituted) cyclopentadienyl group, (substituted) indenyl group, (substituted) azulenyl group or (substituted) fluorenyl group. m is an integer of 1 to 3, and when plural L are present, they may be the same as or different from each other. Plural L may be directly linked to each other or may be linked through a crosslinking group containing a carbon atom, a halogen atom, a silicon atom, a nitrogen atom, an oxygen atom, a sulfur atom or a phosphorus atom. Q is selected from a halogen atom, a hydrocarbon group, an anionic ligand and a neutral ligand capable of coordination by a lone pair in combination with the same or different atom, group or ligand, and n is an integer of 1 to 4.

Examples of the halogen atoms include fluorine, chlorine, bromine and iodine, and examples of the hydrocarbon groups include the same groups as previously mentioned (e.g., alkyl group). Examples of the anionic ligands include alkoxy groups, such as methoxy, tert-butoxy and phenoxy; carboxylate groups, such as acetate and benzoate; sulfonate groups, such as mesylate and tosylate; and amide groups, such as dimethylamide, diisopropylamide, methylanilide and diphenylamide. Examples of the neutral ligands capable of coordination by a lone pair include organophosphorus compounds, such as trimethylphosphine, triethylphosphine, triphenylphosphine and diphenylmethylphosphine; and ethers, such as tetrahydrofuran, diethyl ether, dioxane and 1,2-dimethoxyethane. It is preferable that at least one of Q is a halogen atom or an alkyl group.

Of the metallocene compounds represented by the formula (7), a metallocene compound represented by the following formula (9) or (10) is preferable in the invention.

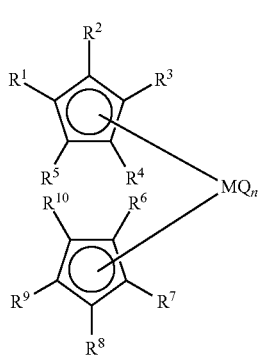

(9)

In the formula (9), M, Q and n are the same as those in the formula (7). $R^1$ to $R^{10}$ are each an atom or a group selected from a hydrogen atom, a hydrocarbon group, a halogen atom-containing group, a heteroatom-containing group and a silicon atom-containing group, and they may be the same as or different from each other.

Examples of the hydrocarbon groups include straight-chain hydrocarbon groups, such as methyl group, ethyl group, n-propyl group, allyl group, n-butyl group, n-pentyl group, n-hexyl group, n-heptyl group, n-octyl group, n-nonyl group and n-decanyl group; branched hydrocarbon groups, such as isopropyl group, tert-butyl group, amyl group, 3-methylpentyl group, 1,1-diethylpropyl group, 1,1-dimethylbutyl group, 1-methyl-1-propylbutyl group, 1,1-propylbutyl group, 1,1-dimethyl-2-methylpropyl group and 1-methyl-1-isopropyl-2-methylpropyl group; cyclic saturated hydrocarbon groups, such as cyclopentyl group, cyclohexyl group, cycloheptyl group, cyclooctyl group, norbornyl group, adamantyl group, methylcyclohexyl group and methyladamantyl group; cyclic unsaturated hydrocarbon groups, such as phenyl group, tolyl group, naphthyl group, biphenyl group, phenanthryl group and anthracenyl group; saturated hydrocarbon groups substituted with cyclic unsaturated hydrocarbon groups, such as benzyl group, cumyl group, 1,1-diphenylethyl group and triphenylmethyl group; halogen atom-containing hydrocarbon groups, such as trifluoromethyl group, chlorophenyl group, fluorophenyl group and trifluoromethylphenyl group; heteroatom-containing hydrocarbon groups, such as methoxy group, ethoxy group, phenoxy group, furyl group, N-methylamino group, N,N-dimethylamino group, N-phenylamino group, pyryl group and thienyl group; and silicon atom-containing groups, such as trimethylsilyl group, triethylsilyl group, dimethylphenylsilyl group, diphenylmethylsilyl group and triphenylsilyl group.

Of the groups represented by $R^1$ to $R^{10}$, neighboring two substituents may be bonded to form a condensed ring. Specifically, there can be mentioned, for example, (substituted) indenyl groups, such as indenyl group, 4,5,6,7-tetrahydroindenyl group, 2-methylindenyl group, 2-t-butylindenyl group, 4,5-benzindenyl group and 4-phenylindenyl group; (substituted) azulenyl groups, such as azulenyl group, 2-methylazulenyl group, 2-ethylazulenyl group, 2-isopropylazulenyl group, 2-phenylazulenyl group, 1,2-dimethylazulenyl group, 4,5,6,7-tetrahydroazulenyl group and 2-methyl-4,5,6,7-tetrahydroazulenyl group; and (substituted) fluorenyl groups, such as fluorenyl group, 2,7-dimethylfluorenyl group, 3,6-dimethylfluorenyl group, 2,7-di-t-butylfluorenyl group, 3,6-di-t-butylfluorenyl group, benzofluorenyl group, dibenzofluorenyl group, octahydrodibenzofluorenyl group, octamethyloctahydrodibenzofluorenyl group and octamethyltetrahydrodicyclopentafluorenyl group.

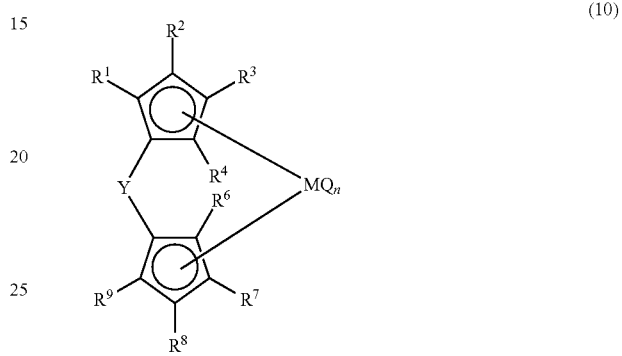

(10)

In the formula (10), M, Q and n are the same as those in the formula (7), and $R^1$ to $R^4$ and $R^6$ to $R^9$ are the same as those in the formula (9). Y is a bonding group to crosslink two conjugated 5-membered ring ligands, and preferably has a structure represented by the following formula (11) or (12).

(11)

(12)

$Y_1$ and $Y_2$ are each carbon or silicon, and $R^{11}$ to $R^{14}$ are each an atom or a group selected from a hydrogen atom, a hydrocarbon group, a halogen atom-containing group, a heteroatom-containing group and a silicon atom-containing group. $R^{11}$ to $R^{14}$ may be the same as or different from each other, and two groups of $R^1$ to $R^4$, $R^6$ to $R^9$, and $R^{11}$ to $R^{14}$ may be bonded to form a ring.

Examples of $R^{11}$ to $R^{14}$ include the same atoms and groups as those of $R^1$ to $R^{10}$.

Examples of the organic solvents used for the preparation of the organic transition metal compound in the invention, preferably a metallocene compound, include the same solvents as in the preparation of the aforesaid organic alkali metal compound.

The transition metal compound represented by the formula (5) and the organic alkali metal compound according to the invention can be brought into contact with each other at a temperature of −80 to 200° C., preferably −20 to 130° C., more preferably −20 to 40° C.

The amount of the transition metal compound represented by the formula (5) used is in the range of 0.8 to 1.5 mol, preferably 1.0 to 1.2 mol, based on 1 mol of the organic alkali metal compound according to the invention.

EXAMPLES

The present invention is further described with reference to the following examples, but it should be construed that the invention is in no way limited to those examples.

Structure and purity of the resulting compound were determined by the use of nuclear magnetic resonance (NMR, GSH-270 manufactured by JEOL Ltd.), field desorption mass spectrometry (FD-MS, SX-102A manufactured by JEOL Ltd.), gas chromatography mass spectrometry (GC-MS, HP6890/HP5973 manufactured by Hewlett-Packard Company), gas chromatography analysis (GC-2014 manufactured by Shimadzu Corporation), etc. Unless otherwise noted, all the examples were carried out using a dry solvent in an atmosphere of dry nitrogen.

Preparation Example 1

Preparation of 5-tert-butyl-1,1,3-trimethyl-1,2-dihydropentalene

In a 1000 ml five neck flask, 24.97 g (204 mmol) of tert-butylcyclopentadiene and 399.04 g of acetone were placed. In an ice water bath, 82.1 g (1.15 mol) of pyrolydine was dropwise added, followed by stirring for 18 hours under reflux. In an ice water bath, 70.91 g (1.18 mol) of acetic acid was dropwise added. From the resulting crude product, the solvent was distilled off under reduced pressure (150 torr, 40° C.), and the resulting product was washed with water, a 5% acetic acid solution, a saturated sodium hydrogen carbonate aqueous solution and a saturated saline solution, followed by drying over magnesium sulfate. After the solvent was distilled off, the remainder was purified by vacuum distillation, whereby 23.4 g of 5-tert-butyl-1,1,3-trimethyl-1,2-dihydropentalene represented by the following formula [1] was obtained. Identification was carried out by a $^1$H-NMR spectrum and a GC-mass spectrometry spectrum (GC-MS). The results of the measurement are given below.

$^1$H-NMR (270 MHz, CDCl$_3$, TMS basis): δ5.87 (s, 1H), 5.79 (s, 1H), 2.94 (d, 1H), 2.10 (t, 3H), 1.27 (s, 1H), 1.21 (s, 9H)

GC-MS: m/Z=202 (M$^+$)

As a result of analysis by gas chromatography, the purity was 95.3%. The yield was 54%.

[1]

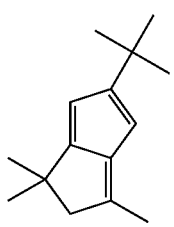

Preparation Example 2

Preparation of 9-(5-tert-butyl-1,1,3-trimethyl-1,2-dihydropentalenyl)-1,1,4,4,7,7,10,10-octamethyl-octahydro-dibenzo[b,h]fluorene In 100 ml three neck flask, 1.58 g (4.09 mmol) of 1,1,4,4,7,7,10,10-octamethyl-octahydro-dibenzo[b,h]fluorene and 30 ml of tert-butyl methyl ether were placed. In an ice/acetone bath, 2.7 ml (4.2 mmol) of a 1.56M n-butyllithium hexane solution was dropwise added. With slowly raising the temperature up to room temperature, the mixture was stirred for 25 hours.

Then, a tert-butyl methyl ether solution containing 0.95 g (4.30 mmol) of 5-tert-butyl-1,1,3-trimethyl-1,2-dihydropentalene was added, followed by stirring for 16 hours under reflux. Thereafter, the reaction solution was poured into 1N hydrochloric acid. The organic layer was separated and washed with a saturated sodium hydrogencarbonate aqueous solution, water and a saturated saline solution. The resulting product was dried over magnesium sulfate, and the solvent was distilled off. The resulting solid was purified by column chromatography and washed with pentane, whereby 9-(5-tert-butyl-1,1,3-trimethyl-1,2-dihydropentalenyl)-1,1,4,4,7,7,10,10-octamethyl-octahydro-dibenzo[b,h]fluorene represented by the following formula [2] was obtained. The yield was 2.03 g and was 84%. Identification was carried out by a $^1$H-NMR spectrum and a FD-mass spectrometry spectrum (FD-MS). The results of the measurement are given below.

$^1$H-NMR (270 MHz, CDCl$_3$, TMS basis): δ7.58 (s, 1H), 7.55+7.54 (s, 1H), 7.50+7.49 (s, 1H), 6.89+6.46 (s, 1H), 6.32+5.93 (s, 1H), 3.87+3.83 (s, 1H), 3.11 (d, 1H), 2.57 (d, 1H), 1.71 (s, 3H), 1.67-1.61 (m, 8H), 1.38-1.28 (m, 27H), 1.18-0.95 (m, 9H), 0.27+0.21 (s, 3H)

FD-MS: m/Z=589 (M$^+$)

[2]

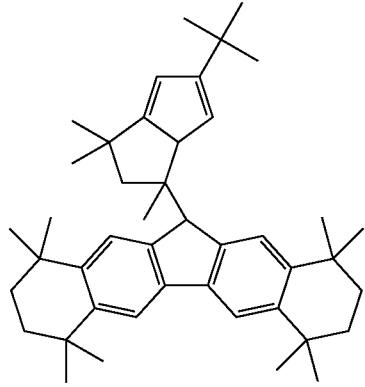

Example 1

Preparation of [9-(5-tert-butyl-1,1,3-trimethyl-1,2-dihydropentalenyl)-1,1,4,4,7,7,10,10-octamethyl-octahydro-dibenzo[b,h]fluorenyl]dilithium In a 30 ml Schlenk flask, 1.18 g (2.01 mmol) of 9-(5-tert-butyl-1,1,3-trimethyl-1,2-dihydropentalenyl)-1,1,4,4,7,7,10,10-octamethyl-octahydro-dibenzo[b,h]fluorene, 0.485 g (4.10 mmol) of α-methylstyrene, 13.5 g of hexane and 2.35 ml (20.2 mmol) of cyclopentyl methyl ether were placed. Then, 2.55 ml (4.21 mmol) of a 1.65M n-butyllithium hexane solution was dropwise added at 26° C., and the mixture was stirred at 70° C. for 3.5 hours, whereby a solution of [9-(5-tert-butyl-1,1,3-trimethyl-1,2-dihydropentalenyl)-1,1,4,4,7,7,10,10-octamethyl-octahydro-dibenzo[b,h]fluorenyl]dilithium was obtained.

The reaction solution was added to methanol-d$_4$ (available from Acrose Co., deuteration ratio: 100%) to deuterate the resulting dilithium salt. After the solvent was distilled off from the resulting solution, the solid precipitated was extracted with chloroform-d, and $^1$H-NMR was measured. The conversion calculated from the values of integral of signals at 3.87 ppm and 3.83 ppm assigned to hydrogen on the fluorene ring was 100%. In the case where signals at 3.87 ppm and 3.83 ppm were not observed, the conversion was considered to be 100%.

Example 2

[9-(5-tert-butyl-1,1,3-trimethyl-1,2-dihydropentalenyl)-1,1,4,4,7,7,10,10-octamethyl-octahydro-dibenzo[b,h]fluorenyl]dilithium was synthesized in the same manner as in Example 1, except that diisopropyl ether was used instead of cyclopentyl methyl ether. The conversion calculated in the same manner as in Example 1 was 100%.

Example 3

[9-(5-tert-butyl-1,1,3-trimethyl-1,2-dihydropentalenyl)-1,1,4,4,7,7,10,10-octamethyl-octahydro-dibenzo[b,h]fluorenyl]dilithium was synthesized in the same manner as in Example 1, except that tert-butyl methyl ether was used instead of cyclopentyl methyl ether. The conversion calculated in the same manner as in Example 1 was 100%.

Example 4

To the solution of [9-(5-tert-butyl-1,1,3-trimethyl-1,2-dihydropentalenyl)-1,1,4,4,7,7,10,10-octamethyl-octahydro-dibenzo[b,h]fluorenyl dilithium obtained in Example 1, 0.547 g (2.35 mmol) of zirconium tetrachloride was added in an ice/acetone bath, and they were allowed to react with each other for 1 hour. Thereafter, the acetone bath was removed, and the reaction was carried out at room temperature for 15.5 hours. The solvent was distilled off, and the soluble matter was extracted with cyclohexane. The resulting solvent was concentrated and allowed to stand still at −20° C. for 30 minutes. The solid precipitated was separated by filtration, washed with hexane and then dried under reduced pressure, whereby [9-(5-tert-butyl-1,1,3-trimethyl-1,2-dihydropentalenyl)-1,1,4,4,7,7,10,10-octamethyl-octahydro-dibenzo[b,h]fluorenyl]zirconium dichloride represented by the following formula [3] was obtained. The yield was 0.507 g and was 34%. Identification was carried out by a $^1$H-NMR spectrum and a FD-mass spectrometry spectrum (FD-MS). The results of the measurement are given below.

$^1$H-NMR (270 MHz, CDCl$_3$, TMS basis): δ7.99 (s, 1H), 7.98 (s, 1H), 7.78 (s, 1H), 7.54 (s, 1H), 6.01 (d, 1H), 5.25 (d, 1H), 3.94 (d, 1H), 2.62 (d, 1H), 2.31 (s, 3H), 1.79-1.61 (m, 8H), 1.57 (s, 3H), 1.43 (s, 3H), 1.41 (s, 3H), 1.39 (s, 9H), 1.35 (s, 3H), 1.32 (s, 3H), 1.28 (s, 3H), 1.24 (s, 3H), 1.09 (s, 9H)

FD-MS: m/Z=748 (M$^+$)

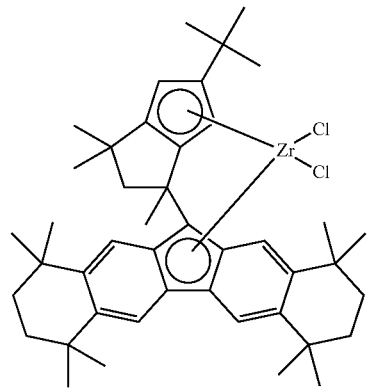

[3]

Comparative Example 1

Preparation of [9-(5-tert-butyl-1,1,3-trimethyl-1,2-dihydropentalenyl)-1,1,4,4,7,7,10,10-octamethyl-octahydro-dibenzo[b,h]fluorenyl]dilithium In a 30 ml Schlenk flask, 1.10 g (2.01 mmol) of 9-(5-tert-butyl-1,1,3-trimethyl-1,2-dihydropentalenyl)-1,1,4,4,7,7,10,10-octamethyl-octahydro-dibenzo[b,h]fluorene, 18.5 g of hexane and 2.65 ml (18.7 mmol) of diisopropyl ether were placed. In an ice/acetone bath, 2.67 ml (4.21 mmol) of a 1.57M n-butyllithium hexane solution was dropwise added, and the mixture was stirred at 70° C. for 5 hours, whereby a solution of [9-(5-tert-butyl-1,1,3-trimethyl-1,2-dihydropentalenyl)-1,1,4,4,7,7,10,10-octamethyl-octahydro-dibenzo[b,h]fluorenyl]dilithium was obtained. The conversion calculated in the same manner as in Example 1 was 85%, and this was lower than the conversion of Example 2 by 15%.

Using the resulting solution of dilithium salt, synthesis of [9-(5-tert-butyl-1,1,3-trimethyl-1,2-dihydropentalenyl)-1,1,4,4,7,7,10,10-octamethyl-octahydro-dibenzo[b,h]fluorenyl]zirconium dichloride was attempted in the same manner as in Example 4. However, the desired product was not observed in the $^1$H-NMR spectrum.

Comparative Example 2

Preparation of [9-(5-tert-butyl-1,1,3-trimethyl-1,2-dihydropentalenyl)-1,1,4,4,7,7,10,10-octamethyl-octahydro-dibenzo[b,h]fluorenyl]dipotassium In a 30 ml Schlenk flask, 0.884 g (1.50 mmol) of 9-(5-tert-butyl-1,1,3-trimethyl-1,2-dihydropentalenyl)-1,1,4,4,7,7,10,10-octamethyl-octahydro-dibenzo[b,h]fluorene and 20 ml of hexane were placed. In an ice/acetone bath, 2.05 ml (3.28 mmol) of a 1.56Mn-butyllithium hexane solution was added. Then, 0.351 g (3.12 mmol) of t-butoxypotassium was added, and with slowly returning the temperature to room temperature, the mixture was stirred for 5 hours to obtain a slurry of [9-(5-tert-butyl-1,1,3-trimethyl-1,2-dihydropentalenyl)-1,1,4,4,7,7,10,10-octamethyl-octahydro-dibenzo[b,h]fluorenyl]dipotassium. The resulting slurry was added to deuterated methanol (available from Acrose Co., deuteration ratio: 100%) to deuterate the resulting dipotassium salt. The conversion calculated in the same manner as in Example 1 using the resulting solution was 88%, and this was lower than the conversion of Example 1 by 12%.

Using the resulting slurry of dipotassium salt, synthesis of [9-(5-tert-butyl-1,1,3-trimethyl-1,2-dihydropentalenyl)-1,1,4,4,7,7,10,10-octamethyl-octahydro-dibenzo[b,h]fluorenyl]zirconium dichloride was attempted in the same manner as in Example 4. However, the desired product was not observed in the $^1$H-NMR spectrum.

Comparative Example 3

In a 30 ml Schlenk flask, 1.18 g (2.01 mmol) of 9-(5-tert-butyl-1,1,3-trimethyl-1,2-dihydropentalenyl)-1,1,4,4,7,7,10,10-octamethyl-octahydro-dibenzo[b,h]fluorene and 19.8 g of hexane were placed. In an ice/acetone bath, 2.67 ml (4.20 mmol) of a 1.57M n-butyllithium hexane solution was dropwise added, and the mixture was stirred for 5 hours under reflux, whereby a solution of [9-(5-tert-butyl-1,1,3-trimethyl-1,2-dihydropentalenyl)-1,1,4,4,7,7,10,10-octamethyl-octahydro-dibenzo[b,h]fluorenyl]dilithium was obtained.

The conversion calculated in the same manner as in Example 1 was 59%, and in addition to the signal of the desired product, signals of several kinds of by-products were observed in the $^1$H-NMR spectrum.

Using the resulting solution of dilithium salt, synthesis of [9-(5-tert-butyl-1,1,3-trimethyl-1,2-dihydropentalenyl)-1,1,4,4,7,7,10,10-octamethyl-octahydro-dibenzo[b,h]fluorenyl]zirconium dichloride was attempted in the same manner as in Example 4. However, the desired product was not observed in the $^1$H-NMR spectrum.

Comparative Example 4

[9-(5-tert-butyl-1,1,3-trimethyl-1,2-dihydropentalenyl)-1,1,4,4,7,7,10,10-octamethyl-octahydro-dibenzo[b,h]fluorenyl]dilithium was synthesized in the same manner as in Comparative Example 3, except that cyclohexane was used instead of hexane and the reaction was carried out at 80° C. The conversion calculated in the same manner as in Example 1 was 69%.

Example 5

Preparation of Diphenylmethyllithium

In a 30 ml Schlenk flask, 0.336 g (2.00 mmol) of diphenylmethane, 0.246 g (2.08 mmol) of α-methylstyrene, 13.2 g of hexane and 2.33 ml (20.0 mmol) of cyclopentyl methyl ether were placed, and the temperature was raised to 50° C. Then, 1.27 ml (2.10 mmol) of a 1.65M n-butyllithium hexane solution was dropwise added at 50° C., and the mixture was stirred at 50° C. for 18 hours, whereby a suspension of diphenylmethyllithium was obtained.

The reaction solution was added to methanol d$_4$ (available from Acrose Co., deuteration ratio: 100%) to deuterate the resulting lithium salt. After the solvent was distilled off from the resulting solution, the solid precipitated was extracted with chloroform-d, and $^1$H-NMR was measured. The conversion calculated from the value of integral of a signal at 3.98 ppm assigned to hydrogen on the methylene carbon was 75%. In the case where the value of integral of the signal at 3.98 ppm corresponded to that of one hydrogen atom, the conversion was considered to be 100%.

Comparative Example 5

Diphenylmethyllithium was synthesized in the same manner as in Example 5, except that α-methylstyrene was not added. The conversion calculated in the same manner as in Example 5 was 10%.

Example 6

Preparation of 2-(2-(dimethylamino)phenyl)-1,1-diphenylethanol

In a 30 ml Schlenk flask, 0.514 g (3.80 mmol) of N,N-dimethyl-o-toluidine, 0.898 g (7.60 mmol) of α-methylstyrene, 6.60 g of hexane and 4.43 ml (38.0 mmol) of cyclopentyl methyl ether were placed. Then, 4.78 ml (7.60 mmol) of a 1.59M n-butyllithium hexane solution was dropwise added at 25° C., and the mixture was stirred for 13 hours. To the reaction mixture, a diethyl ether solution containing 1.34 g (7.50 mmol) of benzophenone was dropwise added, and the mixture was stirred for 30 minutes. The resulting reaction mixture was added to a diethyl ether solution containing 0.500 g (8.3 mmol) of acetic acid, and the mixture was stirred for 5 minutes. Thereafter, 5 ml of water was added, and the mixture was further stirred for 5 minutes. After the aqueous phase was separated, the organic phase was extracted with 10% hydrochloric acid, and the resulting aqueous phase was neutralized, whereby 2-(2-(dimethylamino)phenyl)-1,1-diphenylethanol was obtained as a white crystal. The yield was 0.680 g and was 56%. Identification was carried out by a $^1$H-NMR spectrum. The results of the measurement are given below.

$^1$H-NMR (270 MHz, CDCl$_3$, TMS basis): δ8.54 (s, 1H), 7.40 (d, 4H), 7.30-7.00 (m, 7H), 6.78 (t, 1H), 6.51 (d, 1H), 3.74 (s, 2H), 2.75 (s, 6H)

Comparative Example 6

2-(2-(dimethylamino)phenyl)-1,1-diphenylethanol was synthesized in the same manner as in Example 6, except that α-methylstyrene was not added. The yield was 0.218 g and was 18%.

INDUSTRIAL APPLICABILITY

By the present invention, an organic alkali metal compound is obtained in a high yield. Further, use of the compound obtained by the process makes it possible to prepare an organic transition metal compound which has been difficult to prepare so far, and therefore, the present invention is of industrially great value.

The invention claimed is:

1. A process for preparing an organic alkali metal compound represented by the following formula (3), comprising adding an olefin compound represented by the following formula (2) in the reaction of an active proton-containing compound represented by the following formula (1) with an alkali metal compound in the presence of solvents;

wherein the solvents are a mixture of a hydrocarbon and an aliphatic ether in which the mixing ratio by volume of hydrocarbons/aliphatic ethers is in the range of 95/5 to 85/15;

$$RH_p \qquad (1)$$

wherein R is a hydrocarbon group or an amino group and may contain a halogen atom, a silicon atom, an oxygen atom or a nitrogen atom, H is an active proton, and p is the number of hydrogen atoms abstracted in the reaction with the alkali metal compound,

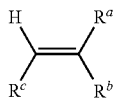 (2)

wherein $R^a$ to $R^c$ are each an atom or a group selected from a hydrogen atom, a hydrocarbon group, a heteroatom-containing group and a silicon-containing group and may be the same as or different from each other, and the neighboring substituents may be bonded to each other to form a ring, $$RN_p \quad (3)$$

wherein R is a hydrocarbon group or an amino group and may contain a halogen atom, a silicon atom, an oxygen atom or a nitrogen atom, N is an alkali metal atom, and p is the same value as in the formula (1).

2. The process for preparing an organic alkali metal compound as claimed in claim 1, wherein at least one of $R^a$ to $R^c$ in the formula (2) is a cyclic unsaturated hydrocarbon group.

3. The process for preparing an organic alkali metal compound as claimed in claim 1, wherein $R^a$ in the formula (2) is an aryl group.

4. The process for preparing an organic alkali metal compound as claimed in claim 1, wherein the alkali metal compound is represented by the following formula (4):

$$AN \quad (4)$$

wherein A is a hydrocarbon group of 1 to 15 carbon atoms, and N is an alkali metal atom.

5. The process for preparing an organic alkali metal compound as claimed in claim 1, wherein the active proton-containing compound represented by the formula (1) is a compound having methine hydrogen or methylene hydrogen as an active proton.

6. The process for preparing an organic alkali metal compound as claimed in claim 1, wherein the active proton-containing compound represented by the formula (1) is a compound containing a cyclopentadiene skeleton having methine hydrogen or methylene hydrogen as an active proton.

* * * * *